United States Patent [19]
Goodman et al.

[11] Patent Number: 5,964,703
[45] Date of Patent: Oct. 12, 1999

[54] EXTRAVASATION DETECTION ELECTRODE PATCH

[75] Inventors: Jack Goodman, Ann Arbor, Mich.; Arthur Zimmet, Centerport, N.Y.

[73] Assignee: E-Z-EM, Inc., Westbury, N.Y.

[21] Appl. No.: 08/957,121

[22] Filed: Oct. 24, 1997

Related U.S. Application Data

[63] Continuation-in-part of application No. 08/924,631, Sep. 5, 1997, abandoned, which is a continuation of application No. 08/491,149, Jun. 16, 1995, abandoned, which is a continuation of application No. 08/323,595, Oct. 17, 1994, abandoned, which is a continuation of application No. 08/182,221, Jan. 14, 1994, abandoned.

[51] Int. Cl.$^6$ ........................................................ A61B 5/04
[52] U.S. Cl. .......................... 600/382; 600/384; 600/393; 600/396; 600/547
[58] Field of Search ..................................... 600/372, 382, 600/384, 386, 393, 396, 506, 547

[56] References Cited

U.S. PATENT DOCUMENTS

| | | |
|---|---|---|
| 4,010,749 | 3/1977 | Shaw . |
| 4,534,756 | 8/1985 | Nelson . |
| 4,729,385 | 3/1988 | Juncosa et al. .......................... 600/547 |
| 4,743,228 | 5/1988 | Butterfield . |
| 4,877,034 | 10/1989 | Atkins et al. . |
| 4,898,576 | 2/1990 | Philip . |
| 5,246,008 | 9/1993 | Mueller .................................. 600/547 |
| 5,334,141 | 8/1994 | Car et al. . |
| 5,353,802 | 10/1994 | Ollmar ................................... 600/547 |

FOREIGN PATENT DOCUMENTS 757 151  9/1980  Russian Federation ............... 600/547

*Primary Examiner*—Ruth S. Smith
*Attorney, Agent, or Firm*—McAulay Nissen Goldberg Kiel & Hand, LLP

[57] ABSTRACT

A medical extravasation device has an electrode patch that can attach to the skin for sensing electrical information. Tissue impedance is calculated from the electrode patch signals. The patch has elongate pick-up electrodes inboard of elongate energizing electrodes. The measuring zone determined by the elongate space between the pick-up electrodes enhances sensitivity and specificity. The presence of an extravasation is determined by interpreting the tissue impedance measurement. The method for determining the extravasation includes a first step of determining a pre-injection baseline measurement of the tissue impedance. Then, the tissue impedance is monitored during the procedure itself. A predetermined amount of change in tissue impedance is determined to indicate an extravasation.

6 Claims, 4 Drawing Sheets

EXTRAVASATION DETECTION ELECTRODE PATCH

REFERENCE TO RELATED APPLICATIONS

This application is a continuation-in-part of application Ser. No. 08/924,631 filed Sep. 5, 1997 now abandoned, which is a continuation of application Ser. No. 08/491,149 filed on Jun. 16, 1995 now abandoned which in turn is a continuation of Ser. No. 08/323,595 filed on Oct. 17, 1994 now abandoned which is in turn a continuation of Ser. No. 08/182,221 filed on Jan. 14, 1994 now abandoned; all of which were titled Extravasation Detection System.

BACKGROUND OF THE INVENTION

This invention relates to a device and method for the detection of extravasation and more particularly to the detection of extravasation of ionic and non-ionic contrast media.

Extravasation or infiltration is a complication related to the use of power injectors during contrast media injection procedures. When an extravasation occurs, contrast is injected into the tissue surrounding the blood vessel, instead of into the blood vessel itself. The causes for extravasation vary, ranging from operator error in placement of the needle to physiological limitations of the blood vessel to tolerate the rate of fluid administration.

Complications related to extravasation may be quite severe and may include tissue necrosis. This may require reconstructive surgery to repair.

Presently, the only method for detecting an extravasation is for the operator to visually observe it. However, by the time an extravasation is visually observable, much of the previously discussed damage may have occurred.

Accordingly, it is an object of the present invention to provide a safe, efficient, inexpensive and reliable means for the early detection of extravasations.

A very large number of contrast media injection procedures are undertaken each year in the United States; something in the order of ten million. Less than 0.2% of these procedures result in an extravasation. Yet the absolute number is substantial because the base number is so large. The occurrence of an extravasation requires that the procedure be terminated and reinstituted. Accordingly, in a normal situation where an extravasation occurs, early detection is important from the point of view of minimizing the impact on the patient, saving time and providing a timely reinstitution of the procedure.

Although extravasation is not life-threatening, when it does occur it causes discomfort to the patient. It requires a great deal of attention from the doctor and usually means that a procedure has to be interrupted. Thus, it is important that any extravasation detection technique avoid a false indication of extravasation.

In relatively rare cases the extravasation can be quite harmful to the patient. Therefore early detection will avoid patient trauma or other injury.

The false detection of an extravasation results in terminating a procedure. Starting the procedure constitutes unnecessary trauma to the patient and expense. Therefore, any detection technique that gives a noticeable number of false indications will not be used by the doctor.

Accordingly, it is important that any detection technique to be acceptable combine an extremely small number of false indications of extravasation coupled with a reasonably high specificity to the extravasation event being detected.

The relatively large number of contrast media injections undertaken coupled with the relatively small percentage of extravasations that occur means that any procedure to be acceptable to the medical profession has to be non-invasive.

It is an accepted fact that any invasive procedure carries with it risks and trauma. They are to be avoided unless the benefit trade-off warrants such.

Thus, in order for an extravasation detection technique to be acceptable in this context, it must meet the following objectives.

First, it has to be inexpensive and be a disposable single use item.

Second, it must be relatively acceptable to the patient. Therefore, it should be non-invasive and create no pain or other patient problem.

Third, it has to be easy for the technician or doctor to use and readily fits within the procedure involved in the contrast media injection routine.

Fourth, and perhaps more importantly, it must provide next to no false indications of extravasation. A false indication would mean stopping a procedure which did not have to be stopped. Thus it follows that the technique must be specific to extravasation and non-responsive to other phenomenon such as the patient moving his or her arm.

Only a device that meets the above criteria (a) will be safe, (b) have technicians and doctors willing to use it, (c) have patients accept it and (d) have it come within the economic requirements of the institution providing the media injection procedure.

BRIEF DESCRIPTION

The present invention relates to an extravasation detection device and a method for the detection of extravasations. The extravasation device is an electrode patch for sensing certain electrical information.

The electrode patch has a body portion which is adapted to be removably affixed to the skin of a patient. Outer and inner pairs of elongated electrodes are deployed along the body of the patch. The inner pair defines a measuring zone which is shaped and dimensioned to encompass the tip of the needle within the zone. The zone is small enough to optimize sensitivity yet large enough to facilitate placement of the patch over the needle tip. When the body of the patch is affixed to the skin of the patient and alternating electrical energy is applied to the outer electrodes, a field is provided which induces a signal in the inner electrodes, which field is a function of the impedance of the tissue of the measuring zone.

Information from the electrode patch is gathered and processed in order to calculate tissue impedance. The presence of an extravasation is determined by interpreting the tissue impedance measurement and, in that way, extravasations can be detected early. The method for determining the extravasation includes a first step of determining a pre-injection baseline measurement of the tissue impedance.

The electrode patch is affixed so that the measuring zone encompasses the tip of the needle. Energizing the outer pair of electrodes induces a signal in the inner pair of electrodes as a function of the impedance of the body tissue in the measuring zone. Tissue impedance is measured during the media injection procedure using the electrical information sensed by the inner pair of electrodes. The characteristics of the change in this impedance from the baseline impedance measurement is determined. This tissue impedance is monitored during the injection procedure. A predetermined characteristic of the change in tissue impedance indicates extravasation.

DESCRIPTION OF THE PREFERRED EMBODIMENT

Figure 1:
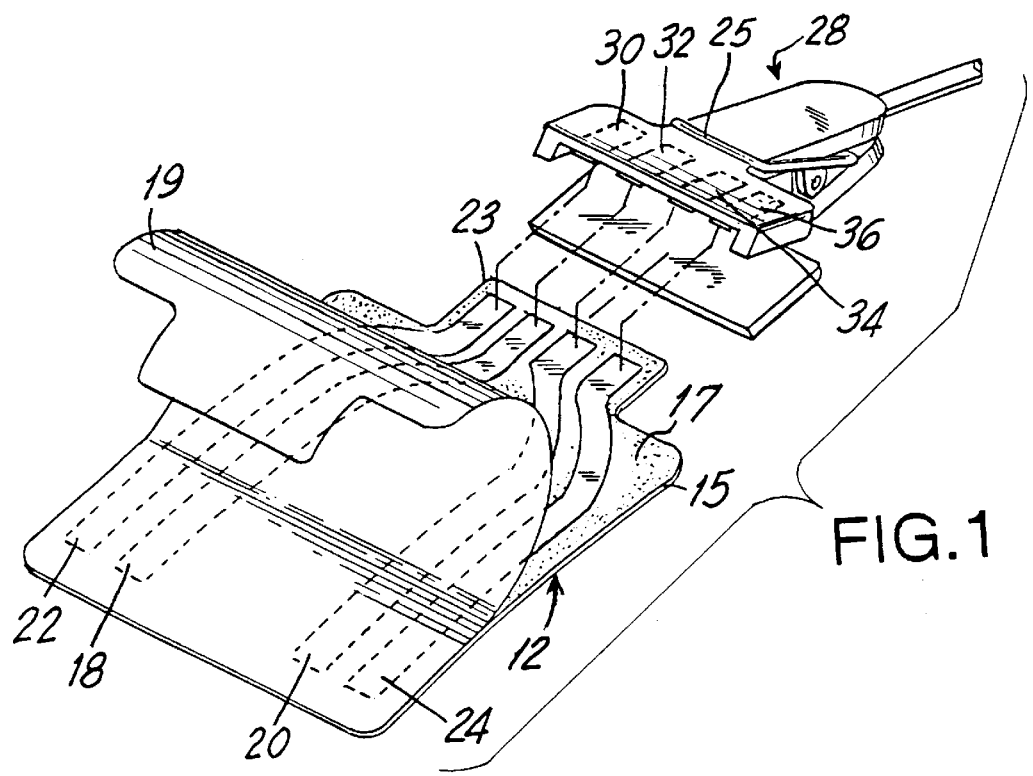
FIG. 1 is an overall perspective view with parts separated of the underside of the preferred embodiment, illustrating the backing paper peeling off the adhesive-backed body of the electrode patch with an open spring clip connector adjacent.

Referring now to the drawings, the reference numeral 10 generally denotes the extravasation detection system of the present invention.

Extravasation detection system 10 includes an electrode patch 12 capable of sensing certain electrical information. Electrode patch 12, as best shown in FIG. 1, includes a PVC body 15 and an adhesive backing 17. Adhesive backing 17 is protected by a clear release backing sheet 19. Electrode patch 12 is formed with four spaced apart electrodes thereon, two inner surface electrodes 18, 20 and two outer surface electrodes, 22 and 24. Between inner electrodes 18, 20 a space 26 is provided. Space 26 is shaped and dimensioned to permit a needle 21 to be placed thereunder and to optimize the sensitivity of the system for the depth of the needle tip within the tissue during a typical injection. By using adhesive backing 15, electrode patch 12 can be easily applied to, and removed from the skin.

Electrode patch 12 is provided with a coupling region 23 shaped and dimensioned to fit within a clip 28. Clip 28 is provided with electrical contacts 30, 32, 34, 36 positioned within the clip so that they can contact surface electrodes 18, 20, 22, 24 when conductor-patch 12 is placed within clip 28. In a preferred embodiment clip 28 includes a spring 25. Clip 28 has electrical leads 50, 52 which connect to a constant alternating current source of power and electrical leads 54, 56 which connects to voltage potential measuring circuitry. Clip 28 further includes a first conduit 27 housing leads 50, 52, 54, 56 which connects to a device 29 which interprets the data sensed by electrode patch 12 and a second conduit 40 which connects to a CT injector 42. Conduit 40 has capability to halt operation of injector 42 in the event an extravasation has been detected or to convey this information to injector 42.

In one embodiment, electrodes 18, 20, 22, 24 are silver/silver chloride strips. Each of the electrodes has a first relatively short vertical section 18a, 20a, 22a, 24a and a second relatively long vertical section 18b, 20b, 22b, 24b. Each electrode has a total length of about 3 inches and a width of about 3/16 of an inch. Inner electrodes 18, 20 are spaced from one another by about 0.75 inches, and outer electrodes 22, 24 are spaced apart by about 1.5 inches.

In that embodiment, the electrode patch 12 has a length of about 3 inches and a width, at its widest point, of about 2 inches.

In use, the extravasation detective system of the present invention works as follows. A syringe needle 21 is introduced into the patient's vasculature. The release backing 19 is removed from the patch body 15 and the electrode patch 12 is then adhered to the patient's skin using adhesive backing 17. As heretofore mentioned, patch 12 is positioned such that the needle tip is covered by the space 26. Electrode patch 12 is clipped into clip 28 via coupling region 23 so that surface electrodes 18, 20, 22, 24 are in contact with electrical contacts 30, 32, 34, 36. Clip 28 is then connected through conduit 27 to impedance monitoring and interpreting circuitry in device 29. The provision of the short vertical sections allows use of one clip for all electrical connections without compromising the spacing of the surface electrodes in the measurement area 26 of the electrode patch 12 where measurements are being made.

Preliminary data is collected to determine the tissue impedance before any injection is made. An injection is then started using injector 42. Continuous calculations of tissue impedance are made during the injection procedure. An extravasation is deemed to have occurred if during the injection procedure the impedance change shows a fairly consistent slope of at least plus or minus 0.5 ohms per second when material is being infused into the vasculature at a rate of more than 0.25 milliliters per second. It is contemplated that, in certain embodiments of the invention, if it is determined that such an extravasation has occurred, there will be an automatic stop mechanism to cease the injection of the media, via conduit 40 or in the alternative some visual or other type of warning signal. Ionic contrast media has a lower impedance than tissue and will cause a decrease in tissue impedance during an extravasation. Non-ionic contrast media has a higher impedance than tissue and will cause an increase in tissue impedance during an extravasation.

In order to have the appropriate data derived from the electrode patch 12 a constant alternating current is applied to the two outer electrodes 22, 24. The current and frequency used is about 200 micro amperes sinusoidal at 20 kilohertz. Inner electrodes 18, 20 provide measurement of voltage potential.

Device 10 provides a method of detecting extravasations. The method includes the steps of determining a pre-injection of baseline measurement for tissue impedance. It also involves the step of determining the amount of change in tissue impedance which indicates an extravasation.

Further, the method involves the step of monitoring tissue impedance during an injection procedure to ascertain if the amount of change previously determined indicates an extravasation has occurred.

The aforementioned method, and system 10, has been used in conjunction with injections of both ionic and non-ionic contrast media to determine the existence of extravasation.

The slope change which is indicative of an extravasation was derived from a series of tests done on animals. Animals were intravenously injected, with both ionic and non-ionic contrast media. Prior to each injection, a measurement of tissue impedance was made and during the course of the injections continuous measurements of tissue impedance were made. It was found that when the injections were intravenous (no extravasation) there was very little change in kin impedance over time. A second series of ionic and non-ionic contrast media were also made.

These injections were deliberately made out of the vasculature to simulate an extravasation. During these injections, a substantial change in tissue impedance occurred almost instantaneously. Tissue impedance was plotted as a function of time to determine the slope change indicative of an extravasation.

Set forth below in Table 1 is a summary of four studies done on doges in the aforementioned manner. Tables 2–5 are the underlying studies summarized in Table 1.

TABLE 1

Summary of Data From Five Dogs

| Variable | I.V. Infusion Ionic Media | Extravasation Ionic Media | I.V. Infusion Non-Toxic Media | Extravasation Non-Ionic Media |
|---|---|---|---|---|
| Resting Impedance | 36 Ohms | 35.2 Ohms | 29.4 Ohms | 32.6 Ohms |
| Slope | 9.1% per minute | −163% per minute | 20.0% per minute | 172% per minute |

TABLE 2

Results of Intravenous Injection of Ionic Contrast in 5 Dogs

| | Dog 1 | Dog 2 | Dog 3 | Dog 4 | Dog 5 | Mean (S.D.) |
|---|---|---|---|---|---|---|
| Leg | L | R | R | L | R | |
| Baseline Resistance | 30 Ohms | 47 Ohms | 29 Ohms | 36 Ohms | 38 Ohms | 36.0 (7.2) |
| Injected Volume | 20 cc | 10 cc | 10 cc | 15 cc | 50 cc | 21.0 cc (16.7 cc) |
| %$\Delta$Z/ml | 0.05 | 0.30 | 0.16 | 0.13 | 0.08 | 0.14 (0.10) |
| $\Delta$Ohms/ml | 0.015 | 0.14 | 0.05 | 0.05 | 0.03 | 0.06 (0.05) |
| %$\Delta$Z/min | 5.4 | 18.0 | 10.0 | 7.5 | 4.6 | 9.1 (5.4) |

TABLE 3

Results of Extravasation of Ionic Contrast in 5 Dogs

| | Dog 1 | Dog 2 | Dog 3 | Dog 4 | Dog 5 | Mean (S.D.) |
|---|---|---|---|---|---|---|
| Leg | L | R | R | L | R | |
| Baseline Resistance | 30 Ohms | 47 Ohms | 30 Ohms | 37 ohms | 32 Ohms | 35.2 (7.2) |
| Injected Volume | 10 cc | 6 cc | 3 cc | 6 cc | 5 cc | 6.0 cc (2.5 cc) |
| %$\Delta$Z/ml | −2.3 | −4.0 | −1.3 | −2.0 | −4.0 | −2.7 (1.2) |
| $\Delta$Ohms/ml | −0.69 | −1.9 | −0.38 | −0.74 | −1.28 | −1.0 (0.6) |
| %$\Delta$Z/min | −140.0 | −240.0 | −75.0 | −120.0 | −240.0 | −163.0 (74) |

TABLE 4

Results of Intravenous Injection of Non-Ionic Contrast in 5 Dogs

| | Dog 1 | Dog 2 | Dog 3 | Dog 4 | Dog 5 | Mean (S.D.) |
|---|---|---|---|---|---|---|
| Leg | R | L | L | R | L | |
| Baseline Resistance | 30 Ohms | 24 Ohms | 27 Ohms | 35 ohms | 31 Ohms | 29.4 (4.2) |
| Injected Volume | 10 cc | 10 cc | 6 cc | 4 cc | 10 cc | 8.0 cc (2.8 cc) |
| %$\Delta$Z/ml | 0.30 | 0.43 | 0.32 | 0.11 | 0.50 | 0.33 (0.15) |
| $\Delta$Ohms/ml | 0.09 | 0.10 | 0.09 | 0.04 | 0.16 | 0.10 (0.4) |
| %$\Delta$Z/min | 18.0 | 26.0 | 19.2 | 6.7 | 30.0 | 20.0 (8.9) |

TABLE 5

Results of Extravasation of Non-Ionic Contrast in 5 Dogs

| | Dog 1 | Dog 2 | Dog 3 | Dog 4 | Dog 5 | Mean (S.D.) |
|---|---|---|---|---|---|---|
| Leg | R | L | L | R | L | |
| Baseline Resistance | 30 Ohms | 24 Ohms | 28 Ohms | 32 ohms | 49 Ohms | 32.6 (9.6) |
| Injected Volume | 5 cc | 5 cc | 3 cc | 4 cc | 3 cc | 4.0 cc (1.0 cc) |
| %$\Delta$Z/ml | 1.4 | 3.0 | 4.0 | 1.9 | 4.1 | 2.9 (1.2) |
| $\Delta$Ohms/ml | 0.41 | 0.72 | 1.12 | 0.60 | 2.0 | 1.0 (0.6) |
| %$\Delta$Z/min | 81.6 | 180.0 | 240.0 | 112.5 | 246.0 | 172.0 (74.0) |

Device 10 and the method associated therewith, although thus far only used to determine extravasations of ionic and non-ionic contrast media, may be useful to determine extravasations of other types of injectable fluids.

One value of the invention is that it involves a non-invasive procedure. Another important consideration is that the electrode configuration adequately encompasses and responds to the extravasation.

During a procedure when the needle is in place within a vein, one cannot visualize exactly where the needle tip is. Since the extravasation occurs at the needle tip, one cannot be certain of where that extravasation will precisely occur along the path of the blood vessel. This invention with its elongated measuring zone 26 (between the pickup electrodes 18 and 20 of FIG. 2) provides the required sensing area.

Figure 2:
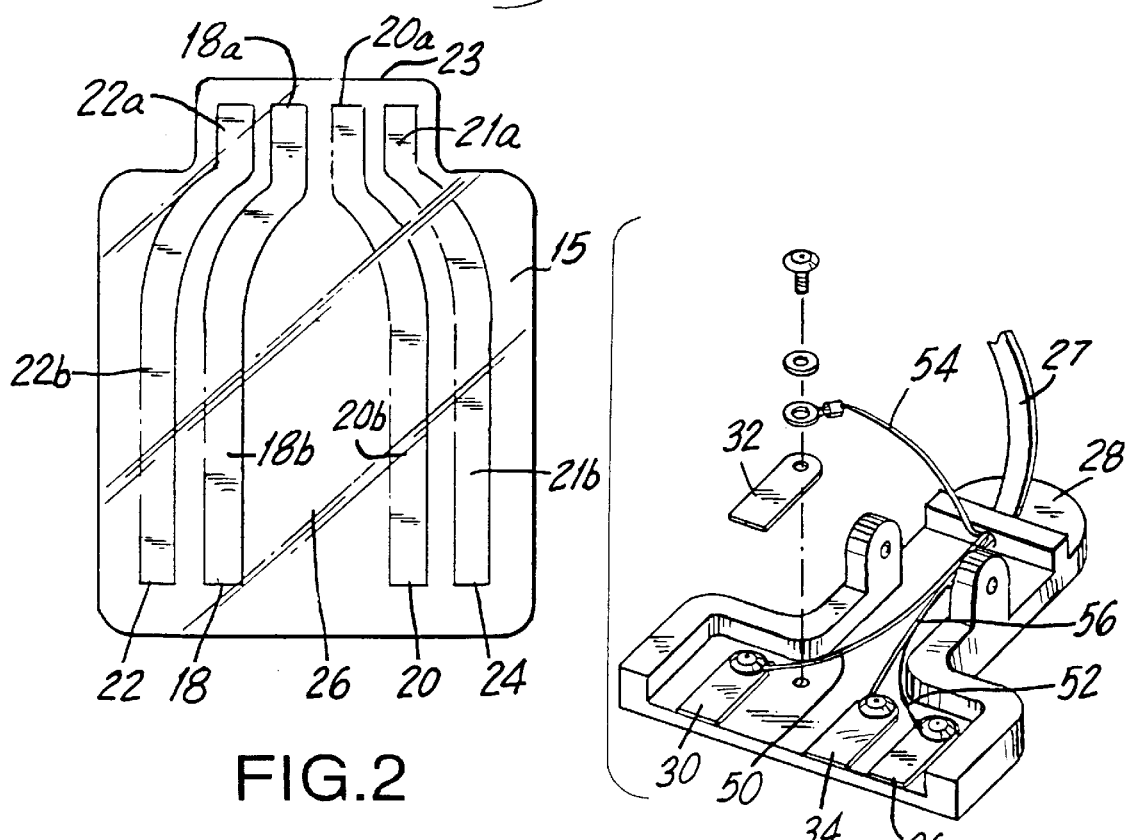
FIG. 2 is a top plan view of the electrode-patch, illustrating the conductive electrode strips within the patch.
Figure 3:
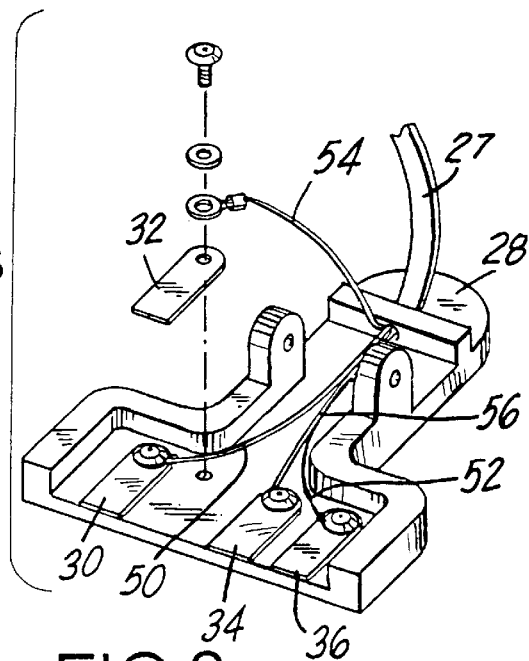
FIG. 3 is a perspective view of the lower jaw of the spring clip connector with a typical contact and hardware exploded off.
Figure 4:
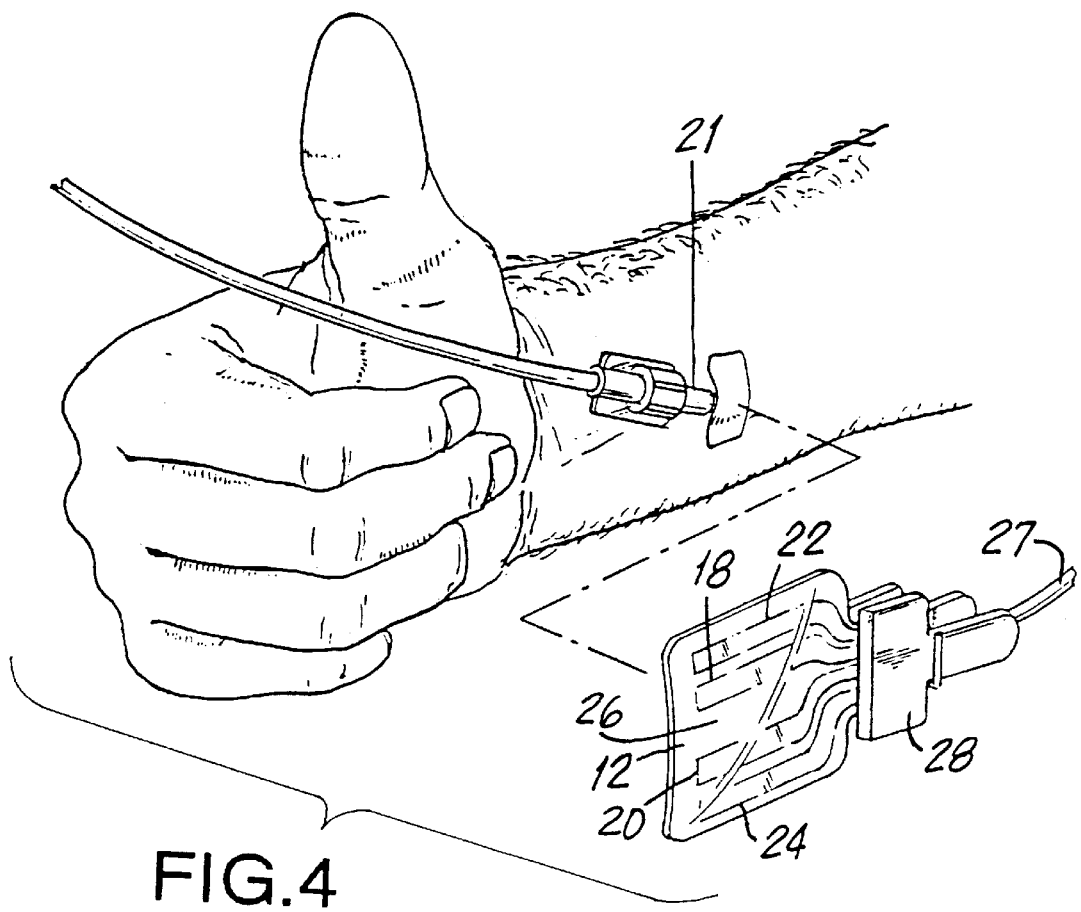
FIG. 4 is a perspective view of a typical method of application, with patch and clip shown prior to placement over the point of needle insertion.
Figure 5:
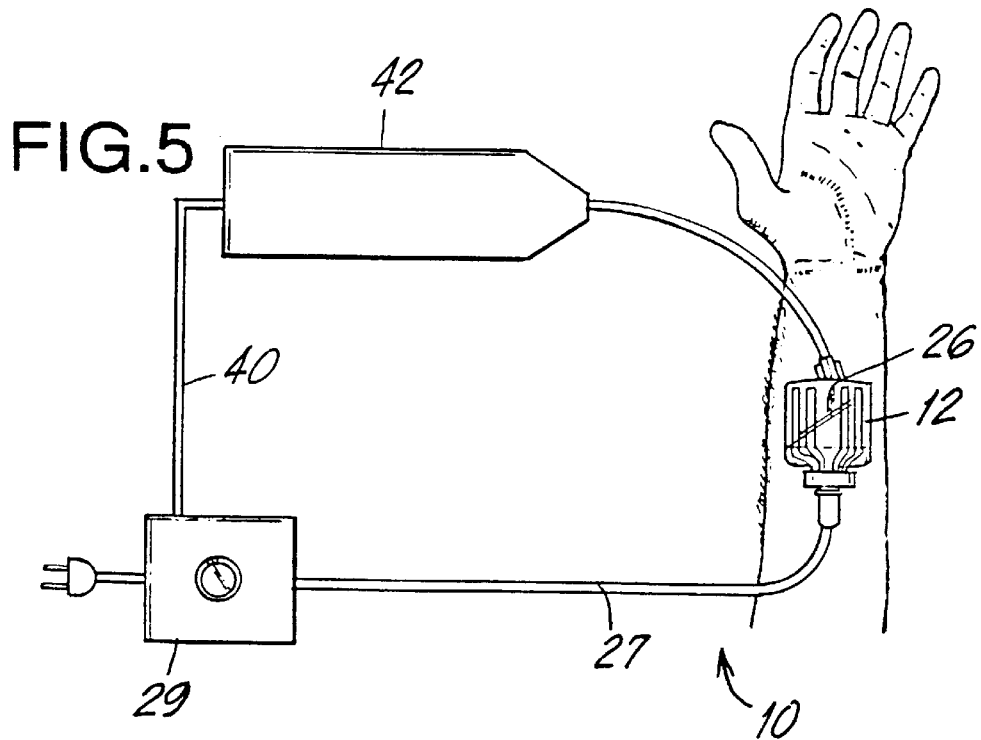
FIG. 5 is a diagrammatic plan view of a typical application and apparatus hook-up.

Furthermore, it is important that these sensing electrodes 18 and 20 have the opening 26 between them that is shown in FIG. 2 so that the zone under that space 26 that is within the patient's body will be sensed if an extravasation occurs.

Figure 6:
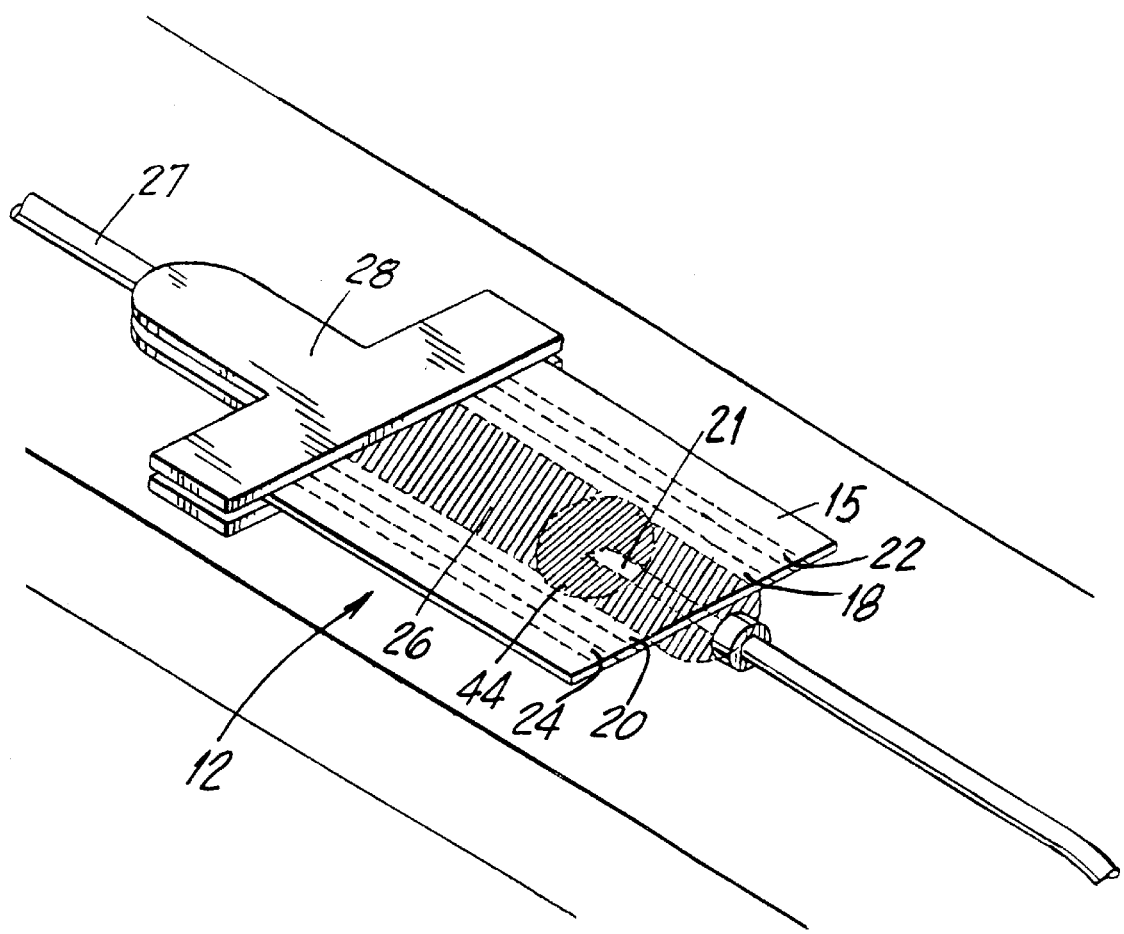
FIG. 6 is a diagrammatic plan view of the patch in place on a patient showing, in idealized form, the relation between an extravasation and the measuring zone.

These elongated sensing electrodes 18, 20 and parallel elongated energizing current electrodes 22, 24 provide the configuration necessary to reliably pickup an extravasation where it occurs. This is illustrated in FIG. 6. Specifically, this sensitivity occurs because applicant's structure assures placement of the electrodes 18, 20, 22, 24 around the point where the needle 21 enters the skin. Thus, the extravasation 44 is substantially centered in the measurement zone that is subtended by the inner electrodes 18, 20. In general, the extravasation will be picked up within ten to twenty ccs of extravasation.

It is the geometric configuration set forth in the above referenced application which meets the objective of providing substantial assurance that an extravasation will be detected yet nearly completely avoid providing a false indication of extravasation.

Figure 7:
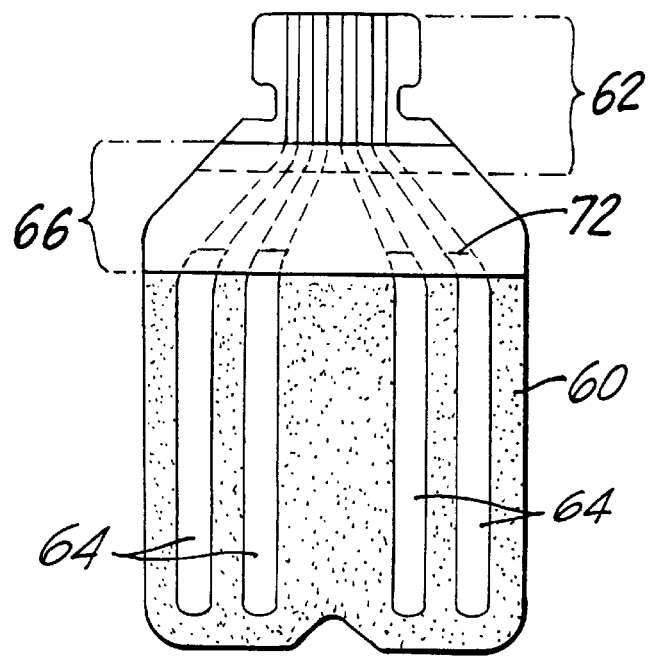
FIG. 7 is a bottom plan view of a presently preferred embodiment of the patch similar to that shown in FIG. 2 except that the clear release liner or ply 68 that is the base or bottom ply is omitted from FIG. 7.
Figure 8:
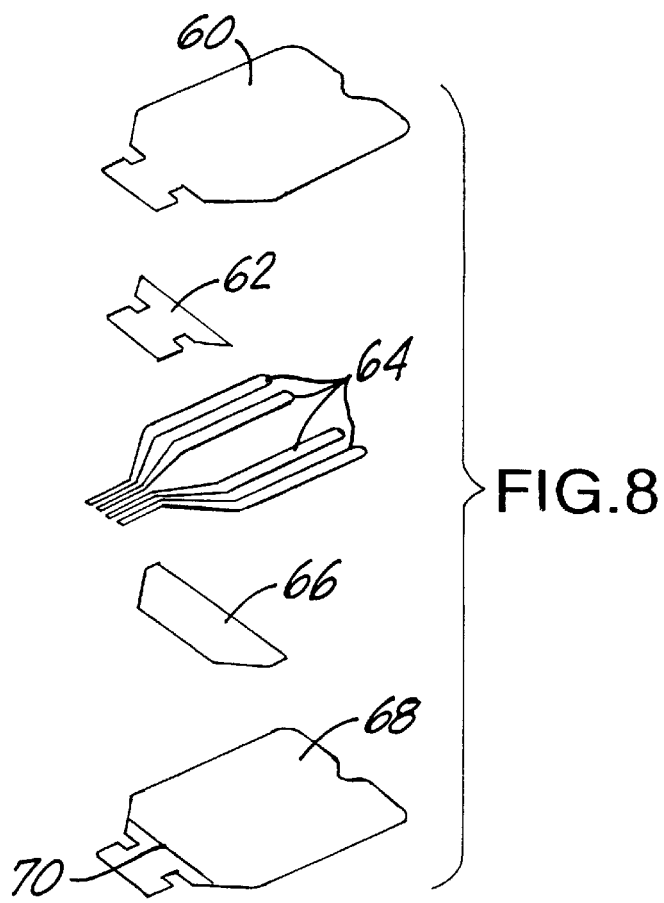
FIG. 8 is an exploded view of the FIG. 7 patch showing the plies and elements which constitute the patch.

FIGS. 7 and 8 illustrate a presently preferred embodiment of the patch. As best seen in the exploded view of FIG. 8, the top of the patch is a clear vinyl ply 60. This ply 60, has on the surface facing the patient, an adhesive which serves to hold the electrodes and to adhere the patch to the patient. Under this vinyl ply 60, there is a reinforcement ply 62 that provides rigidity for the end of the patch that is to be held by the clamp 28 (see FIG. 1). Just below the reinforcement 62, and in large part in contact with and held by the adhesive side of the ply 60 is the set of four electrodes 64. A discussed in connection with FIG. 2, each electrode has an elongate portion. These elongate portions are the active portions for providing the field and for picking up the signal. These electrodes 64 are essentially similar to the electrode arrangement shown in FIG. 1. The patient side of each electrode has a hydrogel coating to assure good contact against the patient's skin. Since this hydrogel is conducting, it is important that the hydrogel coating only be on the electrode and not on any of the surfaces between the electrode since such would tend to short out the signals involved. A clear insulating tape 66 along the short portions of the electrodes has the important function of minimizing interaction between the short portion of the electrodes and the patient so that it is the long portion of the electrodes 64 which are the effective energization and pick up electrodes. Finally, there is the clear release liner 68 having a perforated line 70 that provides the base liner of the patch. As shown in FIG. 1, the release liner (which is the liner 19 in FIG. 1) can be bent back initially so that the patch can be placed into the clamp 28 before it is put into use. Then when it is put into use, the main portion of the liner 68 can be removed by ripping it at the perforation line 70 so that the electrodes 64 can be placed against the patient's skin. The patient side of the vinyl layer 60 has the pressure sensitive adhesive that will adhere the patch firmly to the patient's skin.

FIG. 7 shows the assembly of the FIG. 8 plies with the clear vinyl ply omitted. The overall dimensions are about 3.7 inches by 2.3 inches. The electrodes 64 are each about 0.2 inches wide and the elongate portions are about two inches. The hydrogel coating in the electrodes 64 ends at the line 72. The spacing between the inboard edges of the inner electrodes is about 0.70 inches and the spacing between the inboard edges of the outer pair of electrodes is about 1.5 inches.

What is claimed is:

1. An electrode patch for use in a non-invasive device for detecting extravasation that may occur when a needle with a tip is inserted into a patient in order to introduce fluid into the vascular system of a patient, comprising:

a body of the patch adapted to be affixed to the skin of a patient, an outer pair of elongated electrodes and an inner pair of elongate electrodes, the length of each of said electrodes being deployed along the body of said patch, said inner pair of electrodes being spaced from one another on either side of a center line, said inner pair defining a measuring zone, said measuring zone being shaped and dimensioned to encompass a needle tip within said zone, said zone being small enough to optimize sensitivity, said inner pair being long enough to facilitate placement of the patch over a needle tip inserted into a patient, each of said outer pair of electrodes being outward, relative to said center line, of a respective one of said inner electrodes, energization of said outer electrodes, when said patch is affixed to the skin of a patient, providing a field which induces a signal in said inner electrodes that is a function of the impedance of the tissue in said measuring zone.

2. The patch of claim 1 wherein each of said electrodes further includes a first portion which is relatively short as compared to said elongate portion of each electrode, said relatively short first portions of said electrodes define a coupling region which can be connected to a single clip containing electrical contacts.

3. The patch of claim 1 wherein each of said elongate electrodes are substantially the same length and wherein each of said outer pair of electrodes is adjacent to and spaced from one of said inner pair of electrodes.

4. The patch of claim 3 wherein each of said elongate electrodes has a total length of about 3 inches, and a width of about ³⁄₁₆th of an inch, and wherein said inner pair of electrodes is spaced apart by about 0.75 inches and said outer pair of electrodes is spaced apart by about 1.5 inches, and where said inner pair of electrodes is centralized relative to said outer pair of electrodes.

5. The patch of claim 4 wherein said body is about two inches in width and about three inches in length.

6. The patch of claim 1 wherein said electrodes are silver/silver chloride strips.

\* \* \* \* \*